US00PP25989P3

(12) United States Plant Patent
Shipley

(10) Patent No.: US PP25,989 P3
(45) Date of Patent: Oct. 13, 2015

(54) ***PEDILANTHUS* PLANT NAMED 'CHILLY WILLY'**

(50) Latin Name: *Pedilanthus macrocarpus*
Varietal Denomination: Chilly Willy

(71) Applicant: Nicholas Shipley, Tucson, AZ (US)

(72) Inventor: Nicholas Shipley, Tucson, AZ (US)

( * ) Notice: Subject to any disclaimer, the term of this patent is extended or adjusted under 35 U.S.C. 154(b) by 324 days.

(21) Appl. No.: 13/986,577

(22) Filed: May 16, 2013

(65) Prior Publication Data

US 2014/0345013 P1 Nov. 20, 2014

(51) Int. Cl.
*A01H 5/02* (2006.01)

(52) U.S. Cl.
USPC ..... Plt./302

(58) Field of Classification Search
USPC ..... Plt./302
CPC ..... A01H 5/02; A01H 5/00
See application file for complete search history.

*Primary Examiner* — Kent L Bell

(57) ABSTRACT

A new and distinct *Pedilanthus macrocarpus* named 'Chilly Willy' is characterized by freeze hardiness (at least to 12° F.) beyond that of any cultivars of *Pedilanthus* known to the Inventor. The color of the mature stems is R.H.S. Colour Chart 143A to 143D.

2 Drawing Sheets

Latin name: *Pedilanthus macrocarpus*.
Varietal denomination: Chilly Willy.

BACKGROUND OF THE INVENTION

*Pedilanthus* is a genus of the large plant family Euphorbiaceae. About 15 species of *Pedilanthus* are known from the warm parts of Mexico, ranging in growth form from small shrubs to small trees. The present invention relates to a new and distinct cultivar of *Pedilanthus macrocarpus,* a shrubby succulent species which grows wild in the Sonoran Desert in the Mexican states of Sonora, Baja California Sur and Baja California Norte. Plants have also been found outside the Sonoran Desert in the Mexican state of Sinaloa, south of Sonora. *Pedilanthus macrocarpus* is commonly grown as a succulent landscape shrub in much of the warmer parts of the southwestern United States. Many unpatented clones of *Pedilanthus macrocarpus* are produced and sold in the nursery trade. Until the present time, cultivation of this species has been limited by its minimal frost resistance, with plants showing injury at temperatures between 25 and 30 degrees Fahrenheit (F). The new cultivar was discovered as a naturally occurring stem mutation of an unnamed cultivar growing in a cultivated area near Tucson, Ariz., uninjured by a historic freeze and is the object of this application.

SUMMARY OF THE INVENTION

Among the features that distinguish the new *Pedilanthus macrocarpus* cultivar from all other available and commercial varieties of *Pedilanthus macrocarpus* known to the inventor are the following combination of characteristics: demonstrated freeze hardiness to at least 12 degrees Fahrenheit, upright form and mature stem color (Royal Horticultural Society (R.H.S.) Colour Chart 143A to 143D).

The propagation procedure is as follows: Stems are cut into 3 inch long pieces with at least one node that can be placed below the soil line. Cuttings are set into Carefree Jiffy™ peat substrate without rooting hormone and placed in flats in a standard greenhouse with a minimum nighttime temperature of at least 50 F and warming to up to as warm as 100 F during the day. Rooting is completed within about 8 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Pedilanthus macrocarpus* growing near Tucson, Ariz., depicted in color as nearly correct as it is possible to make in a color illustration of the character.

DETAILED PLANT DESCRIPTION

Figure 1:
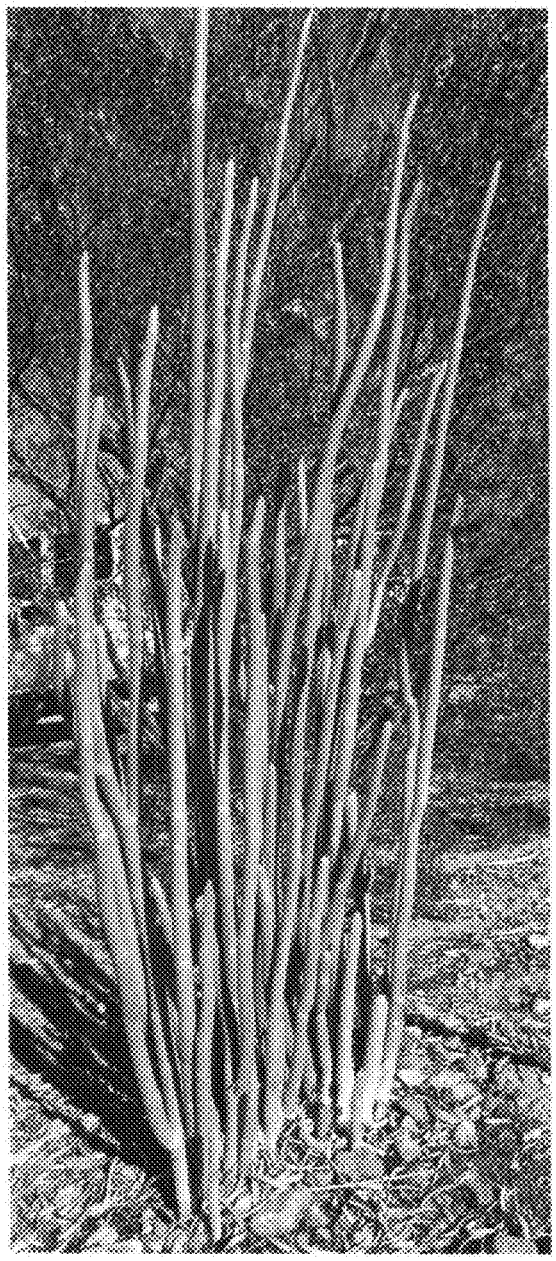
FIG. 1 shows a three year old *Pedilanthus macrocarpus* 'Chilly Willy' growing near Tucson, Ariz.
Figure 2:
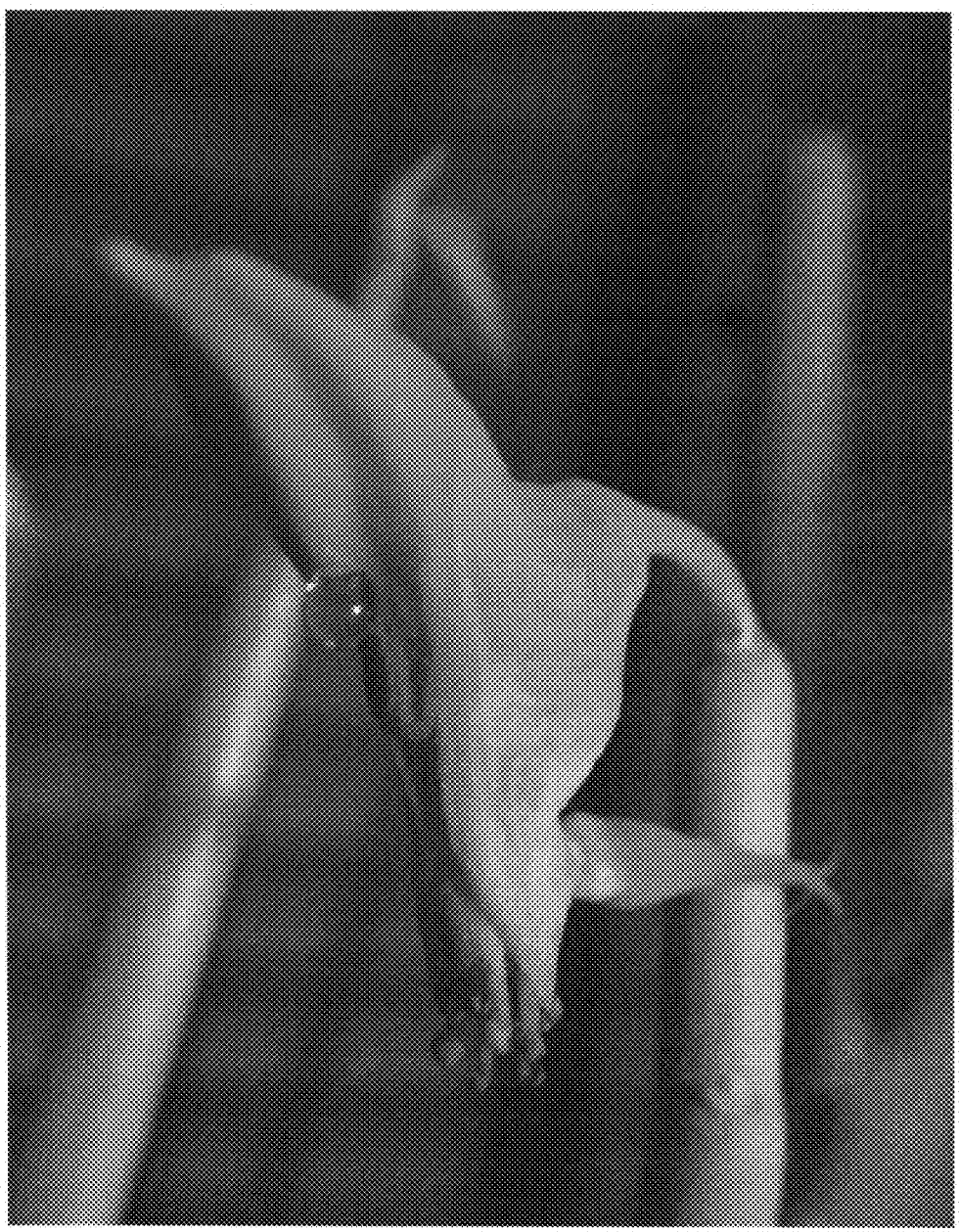
FIG. 2 shows the flowering structure of *Pedilanthus macrocarpus* 'Chilly Willy'.

The following is a detailed description of the new *Pedilanthus* plant based upon one, two and 3 year old plants growing outdoors near Tucson, Ariz. The color descriptions are based upon the 5$^{th}$ edition R.H.S. Colour Chart. Color names other than common usage are as listed in *COLOR Universal Language and Dictionary of Names,* by Kenneth L. Kelly and Deane B. Judd; National Bureau of Standards special publication 440. Washington, D.C.: U.S. Department of Commerce, National Bureau of Standards, December 1976.

Plant name: 'Chilly Willy'.
Species: *Pedilanthus macrocarpus*.
Mature plant size: 5 feet tall×5 feet wide.
Plant growth form: A succulent, mostly leafless shrub with clustered, upright stems. Plant exudes milky sap when injured.
Stems: Terete, constricted at the base of each growth flush, 3-17 mm in diameter; color varies from 143A to 143D on mature stems to 164A on sunward new growth. Stem tips are generally rounded, sometimes acute. Stems when young are covered with fine, appressed woolly hairs, becoming mostly glabrous, scabrous at maturity. The stems are fairly densely covered with slightly raised white (N155D) stomates, approximately 80 μm across.

*Leaf scars*.—Half circular to crescent shaped, the rounded side facing basally, 1 mm high×2 mm wide, containing 3 bundle scars, evenly spaced, color 173C when fresh, weathering to N155A.

Leaves: Alternate, short petiolate-sessile (petioles to 4 mm long), semisucculent, lanceolate, upcurved to upwardly enrolled, 3 mm long×1.5 mm wide to 30 mm long×3-4 mm wide, rapidly becoming caducous with stem maturity or drought. Leaf color varies from 143C on new growth to 53C as leaves become senescent.

*Leaf margins*.—Somewhat undulate, obscurely toothed. Leaf surface: nearly glabrous, with scattered appressed woolly hairs.

Flowering: Inflorescence a highly modified zygomorphic cyathium, more or less shark (crescent) shaped, with the peduncle attachment at the shark's dorsal fin. Cyathia arise from the axils of leaves, usually singly, occasionally paired. Flowering occurs predominantly on the upper portion of the plant, with scattered cyathia elsewhere. Flowering peaks primarily in spring-early summer, although it may occur to some extent throughout the year. The cyathium internally consists of two chambers, a hollow apical nectiferous chamber that leads to a pore on the ventral surface of the cyathium (face of the flower-like structure), where a drop of nectar forms; the second, basal chamber contains numerous unistaminous and one oviferous flower, all of which become exserted from the chamber at maturity. Cyathium measures 32 mm long×7 mm thick, crescent-like in profile, with a basal, more or less obconical bulge (10 mm long×7 mm wide), color 32B. Bulge somewhat radially wrinkled, covered with scattered, mostly appressed, fine, woolly hairs. Bulge offset abaxially from the center by about 15 degrees, obtusely connected to the terminus of the peduncle, the terminus measuring 5 mm high×4 mm wide×2 mm long. Upper lobe of cyathium (color 32B) is dorsally compressed, crestlike, the tip undulate, hollow and nectiferous internally with an adaxial central groove extending from near the distal tip to the bulge. Several secondary grooves (3-4) run parallel to the central grove. The face of the upper cyathium (color 32A-32C) has a central rounded longitudinal ridge, with parallel depressions on either side. The nectar chamber terminates in a pore on the face of the cyathium, just above the central portion of the face where a clear nectar drop accumulates to attract pollinators. The center of the face displays two rounded, grooved, downward facing lobes that form an apparent landing platform (color 179B). Lower lobe of cyathium skirtlike (color grading from 32B to 1C), internally containing the receptacle for the staminous and oviferous flowers, open ventrally on the abaxial side and face, the skirt two sided, deltoid laterally and extending downward, with a rounded tip, margin entire. Interior to the skirt lies another membranous layer with a ciliate margin partially visible on an open cyathium. This membrane is attached to the upper lobe of the cyathium and tapers into a flattened linear structure with a rounded end facing downward inside the cyathium, this structure 7 mm long×2 mm wide, color 62A along the midrib, 62D elsewhere.

*Peduncle*.—Terete, 9 mm long×1.3 mm in diameter, curving from nearly upright to lateral or slightly descending, color 43D, appearing glabrous, slightly waxy, but with scattered, nearly appressed, fine woolly hairs. The unistaminous flowers (about 20) are produced in succession over an extended period, starting just after the exsertion of the female flower. The female flower is exserted basally, just below the peduncle, while the stamens are exserted abaxially, at the basal lobe of the cyathium.

Staminous flowers: Unistaminous, stamens 4.25 mm long at maturity, 1.25 mm×1.25 mm anther (32B), 3 mm long×⅔ mm thick filament (45A); pedicel 14 mm long×⅔ mm thick at maturity, color 62D or lighter. Anthers change to color N92A after dehiscence, shrinking to 1 mm×1 mm. Stamens abscise from pedicels within 2-3 days after anthesis. Pollen color 13D.

Pistillate flowers: Ovary lanceoloid, glabrous, 13 mm long×3 mm thick at anthesis, color apically 43D, near base 43B, basally 3 low ribs, about 4 mm long and ⅓-½ mm wide.

*Base*.—Glandular, the 3 glands alternating with the ribs. Gland color 1D. Ovary connection to pedicel tapered acutely. A ring of color 43C can be seen at this junction. Style glabrous, tapers from 1.5-1 mm×4 mm long, color 43A. Stigma glabrous comprised of 3 conical lobes which vary from apically extended to somewhat reflexed, tapering from 0.3 to 0.4 mm thick×4 mm long and tapering to a point, color 43A. Pistillate flower pedicel hooked, 14 mm long×1.5 mm thick at anthesis, color 149D or lighter, glabrous, obscurely grooved longitudinally (about 10). Fruit a loculicidal 3 seeded capsule. No capsules or seeds were available at the time of description.

COMPARISONS TO RELATED *PEDILANTHUS*

The color seen in *Pedilanthus macrocarpus* stems typically ranges from pale yellow green (192A) to brilliant yellow green (N144B). 'Chilly Willy' stems normally range in color from 143A to 143D on typical stems to 164A on sunward new growth. *Pedilanthus macrocarpus* clones vary from short, very tight, vertically clustered forms to rather rangy, arching forms up to 6 ft or more in height and spread. 'Chilly Willy' is an intermediately sized form, rarely over 5 feet in size, moderately tightly clustered, with only a small tendency to produce arching stems. *Pedilanthus macrocarpus* flowering structures commonly vary in color from 32B to about N30A. The predominant flower color of 'Chilly Willy' is 32B. *Pedilanthus macrocarpus* normally is damaged by temperatures varying from 28° F. to 25° F. Severe damage or death normally occurs when these plants are exposed to temperatures below 20° F. 'Chilly Willy' was selected from a plant that had survived repeated freezes from 13-15° F. without damage. Open grown plants of Chilly Willy have survived with no damage at a documented temperature of 12° F. while other unrelated plants were killed.

I claim:

1. A new and distinct *Pedilanthus macrocarpus* plant substantially as described and illustrated herein.

* * * * *